United States Patent [19]

Guire et al.

[11] Patent Number: 4,826,759

[45] Date of Patent: May 2, 1989

[54] FIELD ASSAY FOR LIGANDS

[75] Inventors: Patrick E. Guire, Eden Prairie; Stephen J. Chudzik, Minneapolis, both of Minn.

[73] Assignee: Bio-Metric Systems, Inc., Eden Prairie, Minn.

[21] Appl. No.: 657,627

[22] Filed: Oct. 4, 1984

[51] Int. Cl.[4] ............... C12Q 1/00; C12Q 1/54; C12Q 1/48; C12Q 1/26; C12Q 1/28; G01N 33/535

[52] U.S. Cl. .................... 435/4; 435/7; 435/14; 435/15; 435/25; 435/28; 435/805; 435/291; 436/74; 436/125; 436/165; 436/169; 436/170; 436/514; 436/518; 436/530; 436/810; 422/56; 422/57; 422/58; 422/61

[58] Field of Search .......... 435/5, 7, 14, 15, 25, 435/28, 288, 291, 805; 436/125, 165, 169, 170, 514, 518, 530, 810, 74, 79; 422/56-58, 61

[56] References Cited

U.S. PATENT DOCUMENTS

| | | | |
|---|---|---|---|
| 3,511,608 | 5/1970 | Anderson | 422/56 |
| 3,644,177 | 2/1972 | Zyk | 435/805 |
| 3,785,930 | 1/1974 | Ellis | 422/56 |
| 4,055,394 | 10/1977 | Friedman et al. | 422/56 |
| 4,254,083 | 3/1981 | Columbus | 422/56 |
| 4,288,228 | 9/1981 | Oberhardt | 422/56 |
| 4,298,688 | 11/1981 | Kallies | 422/56 |
| 4,446,232 | 5/1984 | Liotta | 435/805 |
| 4,459,358 | 7/1984 | Berke | 436/810 |
| 4,587,102 | 5/1986 | Nagatomo et al. | 435/805 |
| 4,603,107 | 7/1986 | Deneke et al. | 435/805 |
| 4,717,656 | 1/1988 | Swanljung | 435/7 |

Primary Examiner—Esther M. Kepplinger
Attorney, Agent, or Firm—Mary P. Bauman; James R. Haller; Gregory P. Kaihoi

[57] ABSTRACT

Apparatuses and methods are disclosed which can be used in the field (i.e., outside the laboratory environment) to determine qualitatively and at least semiquantitatively the presence or absence of minute quantities of ligand. The apparatus can be in the form of a strip comprising a support means provided with a groove intermediate its ends forming a crease line upon which the strip can be folded upon itself with bibulous elements and spaced from the crease line and arranged so that when the strip is folded upon itself the bibulous elements become aligned with each other and come into liquid contact.

17 Claims, 5 Drawing Sheets

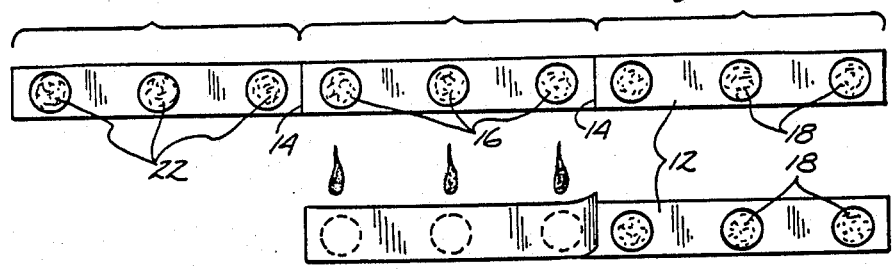
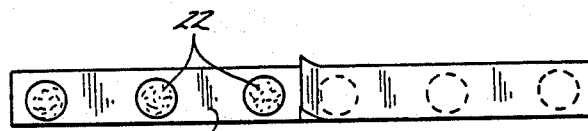
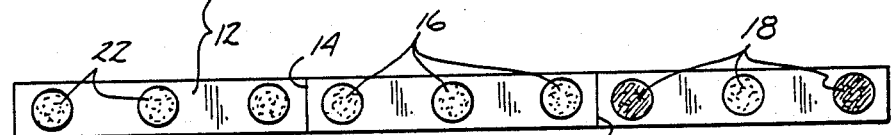
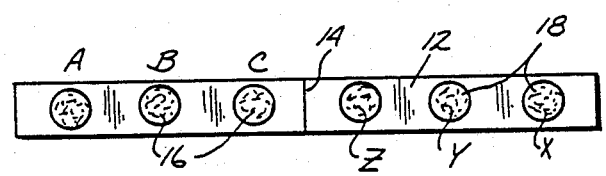
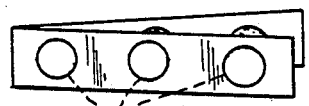
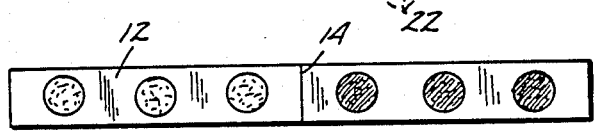

FIELD ASSAY FOR LIGANDS

BACKGROUND OF THE INVENTION

A variety of accurate and reliable assays for measuring minute quantities of analyte dissolved in a solution (e.g., hormones in biological fluids) have been produced and described in the literature. Such assays have commonly required, for their proper performance, a rather high degree of technical and mechanical skill in the measurement of small amounts of reagents, in following detailed procedures, and in using sophisticated analytical equipment. There exists a need for a method of qualitatively and desirably at least semiquantitatively detecting, in the field (that is, outside the laboratory environment) the presence or absence of minute quantities of materials on a rapid basis by persons who often may not be technically skilled. For example, tests for various drug levels in human biological fluids such as urine and blood serum desirably should be available to and capable of use by law enforcement personnel or by paramedics or other emergency medical personnel, inasmuch as it is often of great diagnostic benefit to quickly determine the presence or absence of particular drugs in the blood stream. A ready and effective assay is needed for determining whether certain harmful substances are present in food, such as penicillin in milk, marine toxins in seafood, etc. Needed also are effective field tests for determining whether pollutants exceed particular concentrations (e.g., salts of mercury in lake water).

The present invention provides apparatuses and methods which are unique in that they can in large measure be readily and easily used or performed in the field by minimally trained personnel.

SUMMARY OF THE INVENTION

The present invention provides an apparatus and method for the detection of analytes, the invention making use of first and second normally separated and spaced reaction zones, each comprising a bibulous element. Support means are provided to carry the bibulous elements in a normally spaced relationship, the support means providing means for moving one or both of the bibulous elements in a predetermined path or paths so as to bring them into liquid-transferring contact with one another. Prior to performing an assay with the invention, the bibulous strips are desirably maintained dry and are spaced from one another, as mentioned, by the support means.

In one embodiment, a liquid sample suspected of containing an analyte is added to the apparatus and specifically to the first bibulous reaction zone. Broadly speaking, the first reaction zone may contain a chemical system that responds to the analyte, if any, in the liquid sample to provide a liquid-transferrable chemical species, the presence or amount of which is related to the presence or amount of the analyte. The apparatus may have two, three or more zones. For example, a liquid analyte sample added to a zone may entrain and carry with it another chemical species for ultimate liquid transfer to the first bibulous element. As will now be understood, once the bibulous elements are brought together into liquid-transferring contact, the transferrable detectable chemical species, if any, will be transferred to the second bibulous element, resulting in the production of a detectable signal.

Although the apparatus and method of the invention are applicable, in a broad sense, to a wide variety of analytes and chemical detection systems, in its preferred embodiment, (and particularly when small amounts of an analyte are to be detected), the invention makes use of ligand-receptor pairs. The first reaction zone, in this embodiment, may have bound to it one member ("pair member") of a ligand-receptor group comprising, commonly, a pair or set of pairs. Added to the first reaction zone, in addition to the analyte contained in a liquid sample, is a labeled pair member chosen to bind to the first reaction zone in relation to the quantity of analyte in the liquid sample which binds thereto, the label being part of a signal-producing system. The bibulous element of the second reaction zone may carry a label-detection system that is responsive to the label to produce a detectable signal. The invention, in this embodiment, is used by adding to the first reaction zone the liquid sample and the labeled pair member. The presence or amount of the pair member that remains unbound and hence remains liquid-transferrable in the first reaction zone relates to the presence or quantity of analyte in the liquid sample. One or both of the reaction zones are moved in said predetermined path to bring the bibulous elements into liquid-transferring contact with one another to permit any unbound labeled pair member to transfer to the second reaction zone, the detection system in the latter responding by producing a detectable signal.

DESCRIPTION OF THE DRAWING

FIGS. 5A, B, C and D schematically represent an apparatus of the invention in sequential stages of its use;

FIGS. 6A, B and C schematically represent another apparatus of the invention in various stages of its use;

DESCRIPTION OF PREFERRED EMBODIMENTS

Figure 1:
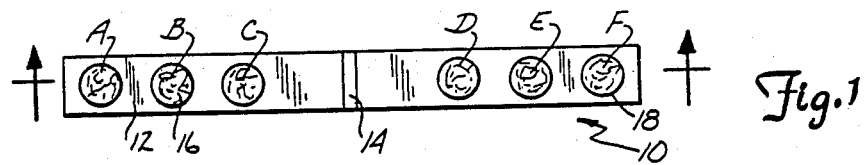
FIG. 1 is a plan view of an apparatus of the invention.

As used herein, "ligand-receptor binding pair" or "ligand-receptor pair" refers to a pair of compounds of which one, a "receptor" is capable of recognizing a particular spacial and polar organization of the other ("ligand") or portion thereof, and is capable of binding to that compound. For various ligands, illustrative receptors forming the other half of a ligand-receptor pair include antibodies, enzymes, lectins, Fab fragments, and the like. Commonly, the receptor will be an antibody and the analyte or analyte derivative will act as an antigen or hapten. As used herein, "analyte derivative" means a chemical derivative of an analyte that retains the capacity to bind to the other member of a ligand receptor pair in competition with the analyte.

By "labeled pair member" or "labeled ligand-receptor pair member" is meant a conjugate of one ligand-receptor pair member with a chemical label such as an enzyme or other detectable chemical species, the conjugate retaining the capacity to bind to the other member of the ligand-receptor pair and the enzyme or other detectable label continuing to have the capacity of being detected by a detector system (which may be a separate chemical reaction system) to provide a perceptible signal. "Detector", "label detector" and the like, refers to a chemical system that provides perceptible signals, commonly electromagnetic radiation or absorption of the same leading to perceptible fluorescence, color changes and the like, when contacted with a specific enzyme or other label.

Speaking broadly, the apparatus and method of the invention may be used with a large variety of known chemical analysis techniques that involve at least two distinct reactions of which one, in a liquid medium, provides a liquid-transferrable chemical species, the presence or amount of which is related to the presence or amount of analyte in a liquid sample that is added to the apparatus. A separate second reaction involves the detection of the transferrable chemical species to produce a detectable signal.

The invention thus is useful for detecting a broad range of analytes that can be suspended or dissolved in a liquid carrier. Such analytes include inorganic elements and their compounds (usually salts), organic monomers and polymers including macromolecules and assemblages thereof such as subcellular organelles (chromosomes, nuclei, chloroplasts, cell membranes), viruses, bacteria, fungi and other microorganisms. Excellent lists of analytes which are part of specific immunological binding pairs are set out in U.S. Pat. Nos. 4,374,925 and 3,817,837, the teachings of which are incorporated herein by reference. Analytes of particular interest include common drugs such as barbiturates and opiates, and various toxins found in food, water and air including natural toxins (microbial, plant, insect, reptillian, etc.) and synthetic (man-made) toxins or poisons. Natural toxins include the marine toxins such as saxitoxin and other paralytic shellfish toxins, ciguatoxin, brevetoxin, palytoxin and the like. Other toxins include mycotoxins (for example, trichothecenes, aflatoxins, patulin, ochratoxins and zearalonone). Synthetic toxins include nerve agents such as Soman (methylphosphonofluoridic acid, 1,2,2-tri-methylpropyl ester) and Sarin (methylphosphonofluoridic acid, 1-methyl-ethyl ester) and pesticides (e.g., Paraoxon (phosphoric acid diethyl-4-nitrophenyl ester), Furadan, 2,3-dihydro-2,2-dimethyl-7-benzo-furanol methylcarbamate, $C_{12}H_{15}NO_3$, a trademarked product of FMC Corporation, and Malathion, [(Dimethoxyphosphinothioyl)thio]butanedioic acid diethyl ester, $C_{10}H_{19}O_6PS_2$ (a product of American Cyanamid).

In the examples that follow, it will be noted that the analytical reactions by and large fall into two broad groups of which one, applicable primarily to inorganic analytes, involves stoichiometric determinations and the other, applicable primarily to organic materials, involves the use of ligand-receptor binding pairs. In the field of stoichiometric inorganic determinations, the invention is particularly applicable to detecting the presence of an analyte in a concentration above a predetermined concentration. For example, it may be desirable to determine whether an analyte that is a pollutant is present in a concentration above a specific upper concentration that may have been set by a regulatory agency. Inorganic stoichiometric determinations are particularly suitable for analyses that involve volumetric precipitation methods, and complexiometric methods including chelatometric techniques such as may be used for metal ion determinations. In general, such analyses provide for a reaction of the analyte in the sample with a stoichiometrically predetermined amount of reagent to provide a liquid-transferrable species, the presence or amount of which is related to the presence or amount of analyte in the sample.

As to the preferred embodiment of the invention which employs ligand-receptor pairs, reference is made to U.S. Pat. No. 4,391,904 which sets forth a variety of binding pairs, the teaching of which patent is hereby incorporated by reference. It will be understood that the invention in its broader aspect is not dependent upon the selection of any particular chemical reaction system, but, being in the nature of apparatus and method, is applicable to a variety of such systems.

The "bibulous elements" that are employed herein may be made of filter paper or other fibrous, particulate or porous material that has the capacity to absorb and be wetted by the liquid of the analyte-containing sample. The bibulous elements provide spatially defined and contained reaction zones within which reactions may occur in a liquid environment. The elements hence should not be soluble in the liquid (normally aqueous solutions) containing the sample. Although the elements may swell somewhat, they should be capable of generally holding their shape against substantial deformation even when saturated with liquid. The bibulous elements need not be flexible or compressible. It is desired, however, that at least the first bibulous element be compressible so that, when it is brought into contact with and pressed against the second element, it will tend to decrease in volume and hence liberate liquid which can then be more readily transferred into the second bibulous element. The first bibulous element in the preferred embodiment desirably includes or is made of a reactive material to which a ligand-receptor pair member can be bound. To promote storageability of apparatuses of the invention, the bibulous elements desirably are not reactive in the dry state with any of the reactants that they contain. The second bibulous element desirably is white or is at least light in color so that color changes or other visually perceptible signals can be readily observed. The bibulous elements may take the form of small discs of filter paper, although fabric, glass wool, polyurethane foams and other materials that can absorb at least small quantities of liquid may be used. The first and second bibulous elements must have exposed or open faces through which liquid may pass when these elements are brought into liquid-transferring contact.

Similarly, the support means which supports the bibulous elements in a normally spaced relationship and which permits them to move in a predetermined path into liquid-transferring contact with one another desirably is of a material which does not react with either the bibulous elements nor the reactants carried by these elements. Preferably, the support means comprises one or more strips or other appropriate shapes of a polymeric material such as polyethylene or polypropylene, the surfaces of which are generally hydrophobic and are not easily wetted with aqueous solutions. Thus, when a support of the type described carries several bibulous elements, each of which may become saturated with a liquid sample, the tendency of liquid to transfer across the surface of the support from one bibulous element to another is reduced.

The size of apparatuses of the present invention may vary as desired. Commonly, however, the bibulous elements may be discs having diameters of, for example, about 6 mm, and the supports that carry bibulous elements desirably are sized to be held in the hand. Although the bibulous elements carried by the support means may be moved into contact with one another through the use of a mechanical device such as a pair of opposed rollers, in its simpler form the bibulous elements are supported by the support means in such a fashion as to permit them to be moved, in the predetermined path, by finger pressure, the elements being gently "pinched" together to cause liquid transfer therebetween. As will be evident from the description that follows, the predetermined path followed by one or both bibulous elements desirably is arcuate or straight. In one embodiment, the first and second bibulous strips may be so oriented as to be brought into liquid-transferring contact when one or both of the elements swell upon the addition of liquid thereto.

Figure 2:
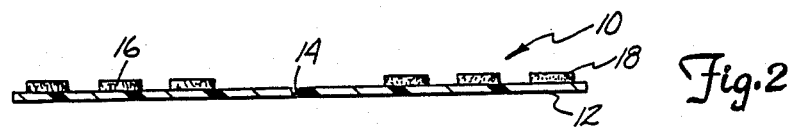
FIG. 2 is a cross-sectional view taken along line 2—2 of FIG. 1.
Figure 3:
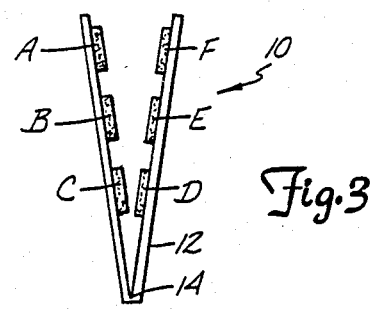
FIG. 3 is a view of the apparatus shown in FIG. 1, folded upon itself.

With reference to the drawing, a simple apparatus of the invention is shown in FIGS. 1-3 and is designated (10). A plastic strip (12), typifying support means, is provided with a groove intermediate its ends forming a crease line (14) upon which the strip can be folded upon itself as shown in FIG. 3. To the upper surface of the strip at one side of the crease line (14) are adhered (by means of adhesive tape having adhesive on both surfaces) first bibulous elements (16), typified as filter paper discs. Similarly adhered to the upper surface of the plastic strip at the other side of the crease line (14) are second bibulous elements (18) typified by filter paper discs. The bibulous elements (16) and (18) are so spaced from the crease line (14) and are so arranged that when the plastic strip is folded upon itself as shown in FIG. 3, the bibulous elements traverse predetermined paths (arcuate, in this example) and become aligned with one another as shown in FIG. 3. Further movement (pinching together) of the elements will bring them into contact with one another, whereupon liquid in the first bibulous elements may be transferred to the second bibulous elements. It will be understood that the apparatus shown in FIGS. 1-3 can be stored in its unfolded condition within a suitable, desirably moisture-proof, envelope of protective material.

In the simple embodiment shown in FIGS. 1-3, a typical test may be made for the presence of NaCl in an aqueous solution such as perspiration.

The detection of NaCl present in body fluids such as perspiration in excess of normal levels is important in the diagnosis of cystic fibrosis. The following example illustrates how the embodiment of FIGS. 1-3 may be employed to determine the amount of NaCl in a given volume of human perspiration. This example also typifies use of the method and device of the invention with inorganic materials using stoichiometrically controlled amounts of reactants, and makes use of standard chemical techniques (the Volhard determination) for determining the presence of chloride ion.

To bibulous elements A, B and C in FIG. 1 are added small quantities of Iron III ammonium sulfate and a predetermined concentration of silver nitrate, except that to bibulous element B is added silver nitrate in substantial excess. Elements D, E and F are identical in that each contains a predetermined concentration of KSCN plus buffer. In addition, bibulous element C is provided with a quantity of sodium chloride in excess of that contained in a given sample volume of normal perspiration.

The test is conducted as follows. Small but predetermined sample volumes of human perspiration containing NaCl are added to each of bibulous elements A, B and C. Chloride ion in the perspiration reacts stoichiometrically with the silver ion, yielding AgCl as an insoluble precipitate; all of the chloride ion in element B, of course, is precipitated due to the excess of silver nitrate in that element. The volume of perspiration added to each of the bibulous elements is enough to thoroughly wet the element and preferably to substantially saturate it.

The apparatus is then folded upon itself as shown in FIG. 3, and the opposing bibulous elements are pinched together to, permit fluid flow between them. As a result (with reference to bibulous elements A and F), fluid transfer causes the ferric ammonium sulfate indicator and any unreacted silver ion to transfer to bibulous element F wherein the silver ion reacts stoichiometrically with the KSCN to yield AgSCN. Any remaining SCN ion reacts with the ferric ion, forming the red $Fe(SCN)^{2+}$. By adjusting the silver nitrate concentrations such that the normal physiological concentration of chloride ion in perspiration precipitates a given amount of silver nitrate yielding a known concentration of free silver ion, and adjusting the KSCN concentration to consume this excess silver ion, the test is adjusted so that the sample containing a normal level of sodium chloride will provide no colored response, whereas the sample with an elevated concentration of sodium chloride will provide a dark red response. Concurrently, the previous addition of NaCl to the bibulous element C provides a red signal in the bibulous element D regardless of the amount of sodium chloride in the patient's perspiration, indicating that the test is operable for large quantities of sodium chloride. Because of the large excess of silver nitrate in element B, no color can form in corresponding element E. Thus, the formation of red signal in element D and of no color in element E provide an indication that the apparatus is operable.

Figures 4, 4A:
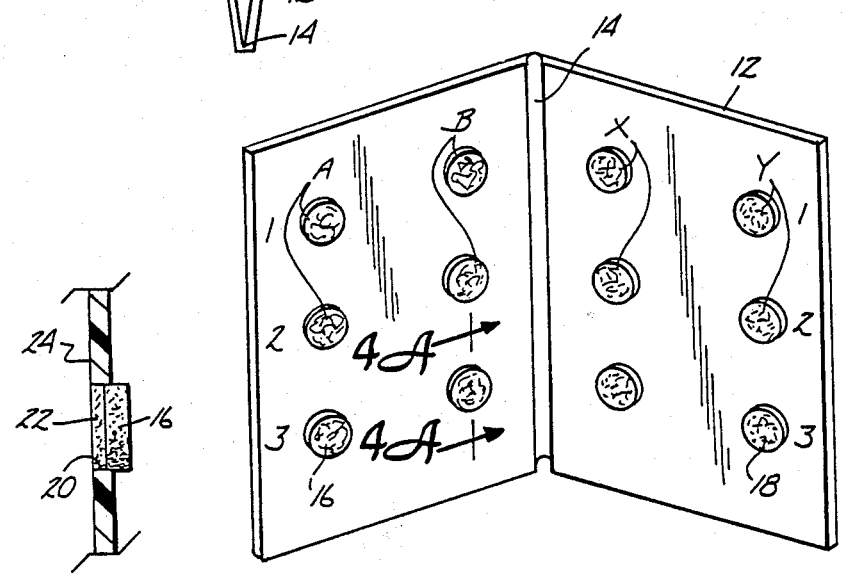
FIG. 4 is a view of a modified apparatus of the invention.
FIG. 4A is a broken-away cross-sectional view taken along line 4A—4A of FIG. 4.

It would be desirable under some circumstances, e.g., involving drug overdoses, to determine which of several common drugs or drug types have been used. For example, one may wish to detect the presence, in urine or blood serum, of barbiturates (e.g., phenobarbital), opiates (e.g., heroin), or tricyclic antidepressants (e.g., nortriptyline). A suitable apparatus for this purpose is depicted in FIGS. 4 and 4A, the apparatus utilizing, as in the previously described apparatus, support means in the form of a plastic strip (12) having a crease line (14) intermediate to its ends to permit the strip to be folded upon itself.

As shown, bibulous elements are carried by the plastic strip, the first bibulous elements being designated generally (16) and the second bibulous elements (18). For ease of description, each bibulous element can further be identified by a letter (designating its vertical column) and a number (designating its horizontal row). The bibulous elements (18) are adhered, in the manner described above, to the plastic strip. The bibulous elements (16), however, are carried in apertures (20) formed in the plastic strip (FIG. 4A). Additional discs (22) of bibulous material are carried by the apertures (20) adjacent the outer surface of the plastic strip and in liquid-transferring contact with the elements 16. In this manner, urine or other liquid suspected of containing a particular drug may be added to the bibulous elements (16) from the outer surface (24) (FIG. 4A) of the plastic strip, the liquid passing through the bibulous element (22) and carrying reactants stored in that element into the bibulous element (16). The bibulous elements in each of rows 1, 2 and 3 are to be used for detecting the drugs phenobarbital, heroin or a heroin derivative, and nortriptyline, respectively. The elements (16) (18), and (22) are prepared by separately impregnating them with aqueous solutions of reactants and then freeze-drying the elements. One surface of each of the elements (18) is then adhered to the strip (12) as described above, and the elements (16) and (22) may be adhered to the plastic strip by means of small pieces of polyester tape bearing adhesive on both sides. The elements (16) and (22) are carried in liquid-transferring contact with one another, as shown in FIG. 4A.

The bibulous elements (18) each were prepared as follows: Approximately 6.3 mm discs of Whatman brand #17 chromatography paper were dried at 105° C. for an hour, cooled in a desiccator, and then transferred to a large tube. To the tube was added one gram of 1,1-carbonyldiimidazole ("CDI") and 35 ml. of dry dioxane, and the discs were rocked for 45 minutes at room temperature. The discs thereafter were washed several times with cold deionized water and again several times with cold 0.1M borate solution, pH 9.0. A solution of 35 ml of the borate solution containing 10 mg of Horseradish Peroxidase was added to the reaction tube and rocked in contact with the discs for 20 hours at 4° C. The discs then were washed several times with cold phosphate-buffered saline solution ("PBS"), and were then stored in PBS at 4° C. A solution of 10% B-D-Glucose, 0.5% polyethylene glycol ("PEG") 4000, and one mg/ml 2,2-azinodi-(3-ethylbenzthiazoline sulphonic acid) was prepared, and 20 microliters of the solution was pipetted onto each of the discs prepared above. The discs were then frozen at −70° C. and lyophilized.

With respect to row 1 (testing for phenobarbital) of the bibulous elements (16), element 1A was prepared as follows: Approximately 6.3 millimeter diameter discs of Whatman #17 chromatography paper were activated by reacting them with CDI as described above, followed by washing with cold borate solution as also described. 1.0 ml. of the anti-phenobarbital IgG fraction of rabbit serum was added to 100 of the thus prepared discs in a 35 ml. 0.1M borate (pH 9.0) solution and reacted for 20 hours at 4° C. The discs were then washed several times with cold PBS and were stored in PBS at 4° C. The 100 discs were blotted lightly and transferred to a lyophilization flask to which was added 2 ml of a 4 mg/ml albumin in 0.5% PEG 4000/PBS solution. The discs were frozen at −70° C. and lyophilized.

Bibulous element 1B was identically prepared, except that 5 micrograms of sodium phenobarbital was added directly to element 1B just prior to the lyophilization step.

The elements (22) used in connection with elements 1A and 1B respectively, were prepared as follows: The sodium salt of phenobarbital was reacted with ethyl-5-bromovalerate, yielding a phenobarbital derivative with a short spacer arm. The ethyl ester was saponified to the free acid and subsequently esterified with N-hydroxysulfosuccinimide through activation with dicyclohexyl carbodiimide. The thus-activated phenobarbital derivative was coupled to glucose oxidase by reaction in an aqueous solution at alkaline pH. The mixture was then fractionated on a diethylaminoethyl (DEAE)-cellulose column, and the fraction with the preferred combination of high enzyme specific activity and high immunological activity was identified by protein determination, enzyme activity determination and radioimmune equivalence assay. The thus purified glucose oxidase-phenobarbital conjugate is appropriately diluted with 1% PEG and 2 mg./ml. ovalbumin in PBS and applied to filter paper discs, the discs then being freeze-dried at −70° C.

The bibulous elements (16) found in rows 2 and 3 for the drugs heroin and nortriptyline were prepared in a similar manner, as were the respective elements 22.

The embodiment of FIGS. 4 and 4A may be used, as by a police officer or ambulance attendant, by adding a single drop of urine suspected of containing one of the three drugs onto the rear side of each of the positions containing elements (16). The liquid sample dissolves and carries with it into the bibulous element (16) the enzyme-labeled analyte carried by the elements (22).

After two minutes, the plastic strip (12) is folded upon its crease line (14), the bibulous elements (16) traveling in predetermined arcuate paths to come into facing engagement with the respective bibulous elements (18). The contacting elements are pinched together momentarily to transfer liquid from the elements (16) to the elements (18), following which the apparatus is again opened and the elements (18) are observed for the development of color. In each case, the bibulous elements in column X should develop a dark color indicative of the presence of predetermined amounts of the respective drug in the elements in column B. The presence or absence of color in the discs in column Y indicate the presence or absence of the respective drug in the urine of the patient. If the plastic strip (12) defining the support means is transparent, then the color changes in the elements (18) can be viewed from the outer surface of the plastic strip.

Referring now to the embodiment shown in FIG. 5, a strip of plastic typifying the support means again is designated as (12). Two grooves, forming crease lines (14) are provided to divide the strip into three substantially equal length sections, designated X, Y and Z respectively. Apertures are formed in the section "X", and discs containing different, predetermined quantities of the phenobarbital-glucose oxidase conjugate exemplified as (22) in FIG. 4A are positioned within the apertures. The elements (16) in section Y are identical to element 1A as described in connection with FIG. 4. The elements (18) in section Z are identical to elements 1X and 1Y described above in connection with FIG. 4.

The embodiment thus described is used by first bending Section X onto Section Y as shown in FIG. 5B so that the elements (22) come into contact with the elements (16). A sample of a unknown liquid, e.g., urine, is then added to each of the elements (22), the liquid flushing the varying quantities of the phenobarbital-glucose oxidase conjugate into the bibulous elements (16). Section X is then unfolded from Section Y, and after a few minutes, Section Z is folded onto Section Y as shown in FIG. 5C, the contacting elements being momentarily pinched together to transfer liquid to the bibulous elements (18). Section Z is then again unfolded, as in FIG. 5D, and the elements (18) are observed to see which, if any, change color. Phenobarbital in the urine will cause one or more of the elements 18 to become darkly colored within several minutes in accordance with the amount of this drug in the urine sample and depending upon the quantity of phenobarbital-glucose oxidase in the elements 22.

Referring now to the embodiment of FIG. 6, a plastic strip (12), provided with a crease line (14), bears on one side first bibulous elements (A) and (B), identical to the bibulous element described above as (1A) in connection with FIG. 4. The strip (12) also bears, on the other side of the crease line, bibulous elements (X), (Y) and (Z), each of which is identical to bibulous element 1Y described above in connection with FIG. 4. The bibulous strips (16) are each provided with a separate bibulous element (22) also as described in connection with FIG. 4A. The bibulous element (C) contains, instead of anti-phenobarbital antibodies, anti-glucose-oxidase antibodies immobilized thereon in sufficient quantity to bind all of the glucose oxidase phenobarbital conjugate in the adjacent element 22. The elements (22) adjacent elements (A) and (B) contain, however, different quantities of the conjugate with element (B) containing substantially less of the conjugate then element (A). The addition of a small sample of urine suspected of containing phenobarbital to each of the elements (16) results in the presence of liquid-transferrable phenobarbital-glucose oxidase conjugate in element (A) if only a small concentration of the drug is present. Higher concentrations of the drug will also provide transferrable conjugate in the element (B). However, the presence of liquid transferable conjugate in element (C) depends upon the activity of the anti-glucose oxidase antibody therein. Assuming that the anti-glucose oxidase antibody and the anti-phenobarbital antibody become deactivated over time at about the same rate, the transfer of the phenobarbital-glucose oxidase conjugate from element C into element (Z) (as indicated by the resultant color change) signals that the apparatus no longer is properly functioning.

When the plastic strip is folded along the crease line (14) and the respective, facing bibulous elements are momentarily pinched together, approximately equal quantities of liquid are transferred from elements (A), (B) and (C) to respective elements (X), (Y) and (Z). Bibulous element (X) will change color in the presence of even small amounts of phenobarbital in the urine specimen. Larger concentrations of phenobarbital in the urine will cause a color change in element (Y) also.

Figure 7:
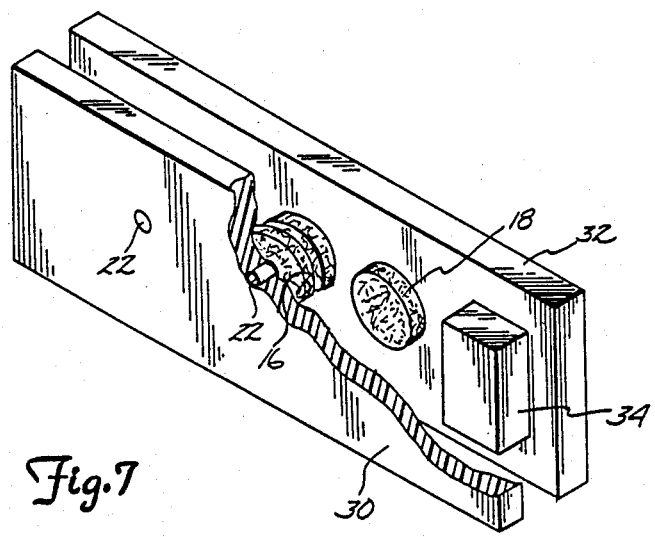
FIG. 7 is a broken-away, perspective view of a portion of another embodiment of an apparatus of the invention.
Figure 9:
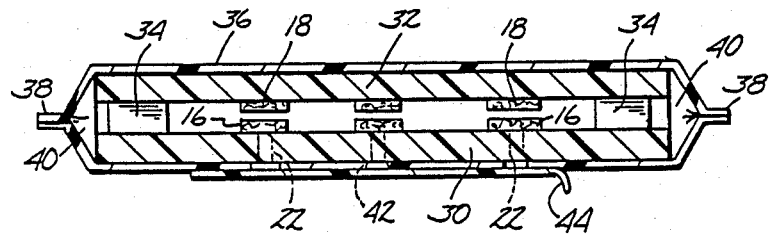
FIG. 9 is a cross-sectional view taken along line 9—9 of FIG. 8.

A particularly preferred embodiment of the invention is shown in FIGS. 7–11. Plastic strips (30) (32), of which at least the latter desirably is transparent, are positioned in parallel, spaced orientation as shown in FIG. 7, and resilient spacers (34) positioned at their ends enable the strips to be pinched resiliently together. Carried on the inner surface of the strip (32) are second bibulous elements (18) of the type described above. Carried on the inner surface of the strip (30) are first bibulous elements (16), also as described above and aligned with the respective bibulous elements (18). The strip (30) may be provided with apertures through its thickness aligned with the bibulous elements (16), and third bibulous elements (22), also as described above, but shaped to fit snugly within the apertures, are also provided in contact with the bibulous element (16). The chemical reagents, for the purpose of this example, will be considered to be the same as those described above in connection with FIGS. 4 and 4A. The plastic strips (30), (32) and the spacers (34), together typifying support means, may be enclosed in a flexible, water-proof, sealed enclosure typified by the plastic wrapper shown in FIG. 9 as (36), the wrapper being generally tubular and being crimped at its ends (38) to form expandable pleats (40), as depicted generally in FIG. 9. The wrapper (36) may be provided with apertures (42) (FIG. 8) which, desirably, are larger than the apertures formed through the strip (30) and which are generally aligned with the latter apertures to enable a liquid sample to be added directly to the bibulous element (22) from outside of the wrapper. The wrapper similarly is desirably transparent. A removable cover, preferably a strip of adhesive tape (44), covers the apertures (42) and can be stripped away when access to the apertures is desired. The wrapper (36) desirably is air-tight and waterproof. When the adhesive strip (44) is in place, the wrapper and tape provide a waterproof and vaporproof enclosure enabling the device to be stored for long periods of time.

Figure 10:
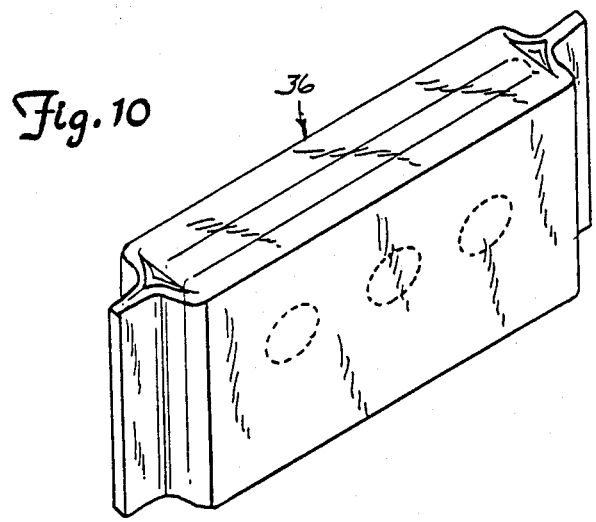
FIG. 10 is a perspective view similar to that of FIG. 8 but taken from the opposite side.

As thus described, the device may be employed in a dip test procedure in which the device is to be dipped into a liquid sample such as milk or urine suspected of containing an analyte. First, the strip of tape (44) is peeled away and discarded and the apparatus is immersed just below the surface of the liquid sample for a period sufficient to enable the bibulous strips (16) to become saturated with liquid. This occurs rapidly, commonly within a second or two. As previously mentioned, the surface of the plastic strips is desirably hydrophobic in nature, and tends to prevent liquid from flowing from one bibulous element to another. The device is removed from the liquid sample, blotted, and is permitted to stand for a few minutes as with the device of FIG. 4. Using finger pressure, the strips (30), (32) are momentarily pressed together causing the bibulous elements (16), (18) to traverse predetermined, straight-line paths into contact with one another. Liquid is transferred from the elements (16) to the elements (18). The latter bibulous elements (18) may then be observed through the transparent plastic wrapper (38) and the transparent strip (32), as depicted in FIG. 10.

Figure 11:
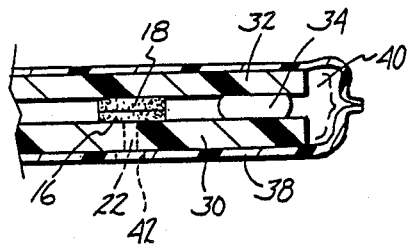
FIG. 11 is a broken-away, cross-sectional view similar to that of FIG. 9 but showing a step in the use of the device shown therein.

Bearing in mind that pinching of the strips (30), (32) together tends to reduce the air volume within the wrapper (38), and hence would tend to raise the air pressure within the wrapper and to force liquid outwardly through the bibulous elements (22), the wrapper desirably is provided with pleated ends or with other expandable structure so that when the elements are pinched together, as shown in FIG. 11, the pleat (40) or other structure expands (such expansion being shown in an exaggerated manner in FIG. 11) such expansion avoiding substantial internal pressure increases.

Figure 8:
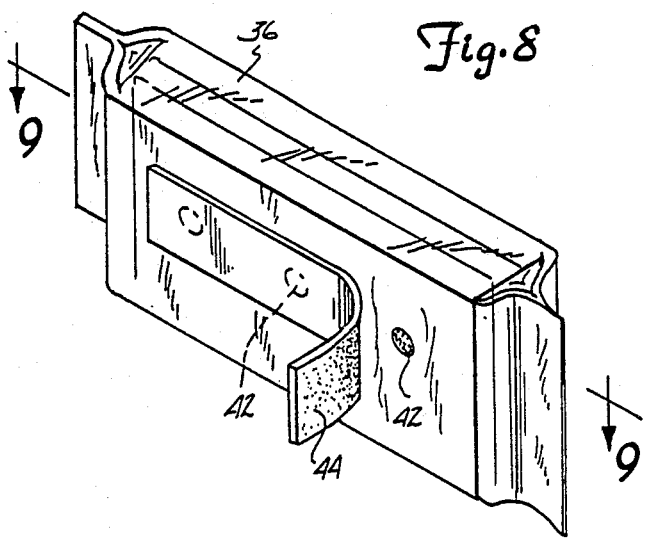
FIG. 8 is a perspective view of the completed apparatus of FIG. 7.

In the method in which the device of FIG. 8 is dipped into a liquid sample, it will now be understood that the volume of liquid sample that enters the device is strictly and fairly accurately limited by the ability of the elements (16) and (22) to absorb liquid; once the elements have been saturated with liquid sample, no further liquid enters. Also, when the bibulous elements (16), (18) are brought into contact with one another during the pinching operation, the elements (18), being initially dry, tend to rapidly absorb moisture from the elements (16). Desirably, when the elements (16) and (18) are pinched together, their aggregate volume is greater than the non-compressed volume of the element (16). In this manner, the leakage of liquid from one bibulous element to another is restrained.

If desired, gaskets may be provided on the inner surfaces of one or both of the plastic strips to surround and isolate the respective bibulous element pairs so that when the elements are pinched together, the gaskets prevent the passage of liquid from one bibulous element to a neighboring bibulous element on the same plastic strip. The gaskets desirably are of a compressible material that may be identical to that of the spacers (34), and, as elements of the support means, may serve as means normally spacing the bibulous elements (16), (18) from one another. If desired, the gasket material may be absorbant of liquid; in this embodiment, as the plastic strips (30), (32) are pressed together, the absorbant, resilient gasketing material also would be flattened to some extent, momentarily reducing its ability to absorb liquid and improving its ability to prevent the flow of liquid therethrough. When the force pressing the plastic strips together is removed, the gasketing material, largely regaining its former shape, would commonly absorb any liquid with which it had come into contact, preventing spread of that liquid to other bibulous elements. As will now also be evident, the spacers (34) and gaskets, if any, may also serve to limit the pinching pressure that can be brought to bear upon the bibulous element (16) and (18).

Although the apparatus of the invention has thus far been described as being capable of manual movement to bring bibulous strips into contact with one another, it will be understood that the bibulous elements can be moved by various other mechanisms as well. For relatively large apparatuses of the type shown in FIG. 4, care must be taken to insure that each of the bibulous elements (16) comes into liquid-transferring contact with its related bibulous element (18). For this purpose, a mechanism may be employed to insure that the halves of the plastic strip (12) are uniformly pressed together. Various mechanical devices may be employed for this purpose; for example, one may employ a pair of squeeze rollers through which the folded-up apparatus of FIG. 4 may be passed. With reference to the embodiment of FIG. 8, the bibulous elements (16) may be made of a material that swells as it absorbs liquid—e.g., a crimped paper or polymeric sponge. Upon addition of a liquid sample, sufficient swelling occurs to bring the elements (16), (18) into contact automatically at the desired time.

Figure 12A:
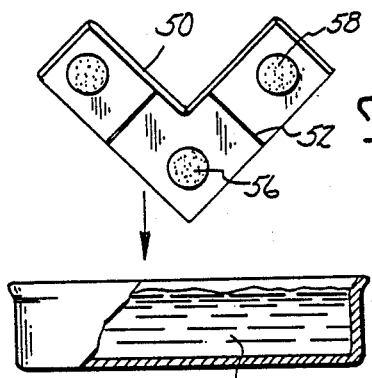
FIG. 12A is a top diagramatic view of another embodiment of an apparatus of the invention, suitable for dipping into a liquid sample.
Figure 12B:
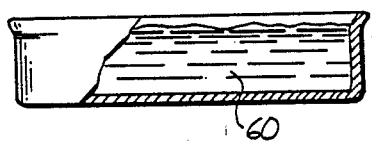
FIG. 12B is a side view of the embodiment shown in FIG. 12A.

Referring now to FIG. 12, a simplified device of the invention may be employed also in procedures in which the apparatus is to be dipped into a liquid suspected of containing a particular analyte. In this embodiment, a generally V-shaped strip of plastic or other material, shown as (50), may be employed as the support. Grooves or the like are provided across the legs of the strip to provide crease lines (52). Bibulous elements (54) and (58) are mounted near the ends of the legs of the device, as shown, and a third bibulous element (56) is mounted at the apex of the "V", the bibulous elements and crease lines (52) being so arranged as to permit the strip legs to bend and carry the bibulous elements (54) and (58) in an arcuate path into contact with the bibulous element (56).

As an example of the use of the embodiment of FIGS. 12-15, the bibulous element (56) may be identical to the bibulous element (16) shown at location 1A in FIG. 4, this element containing bound antiphenobarbital antibody. The disc (54) may be identical to bibulous element (22) shown in FIG. 4A and corresponding to position 1A in FIG. 4, this element containing enzyme (glucose oxidase)-labeled phenobarbital. The bibulous element (58) may be identical to element (18) shown at location 1F in FIG. 4, this element containing the "readout" detection system described in connection with that bibulous element.

Figure 13:
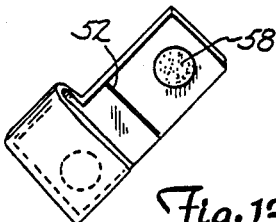
FIG. 13 is a perspective view of the device shown in FIG. 12 and depicting one step in the analysis process.
Figure 14:
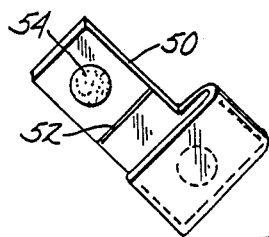
FIG. 14 is a view similar to that of FIG. 13 but showing another step in said process.

In use, the device of FIG. 12 is held as shown and the bibulous element (56) is momentarily dipped into a liquid sample (60) suspected of containing an analyte, in this case, phenobarbital, the sample (60) being, for example, urine. The apparatus of FIG. 12 is immediately removed from the liquid sample, bibulous element (56) having become saturated with the liquid, and the bibulous element (54) is then bent over into contact with the element (56), as shown in FIG. 13, finger pressure being used to assure liquid transfer between the two elements. Liquid from the bibulous element (56) enters the bibulous element (54), bringing the enzyme-labeled phenobarbital material into solution, the phenobarbital moiety of the test sample (60) and the enzyme-labeled phenobarbital competing for antibody binding sites carried by element (56). After several minutes, the bibulous element (54) is lifted from the element (56), and the other bibulous element (58) is brought into contact with the element (56), as shown in FIG. 14. The elements (56) and (58) are pinched together momentarily, following which the element (58) is unfolded and observed for a color change.

Figure 15:
FIG. 15 is a view similar to FIGS. 13 and 14 but showing said steps being carried out simultaneously.

If desired, the bibulous element (54) may first be placed in contact with the bibulous element (56), as described above, and, after a short period of time, the leg of the device supporting the element (58) may additionally be folded down as shown in FIG. 15, placing all three of the elements in liquid-transferring contact. In this embodiment, of course, the element (56) is to be held in an aperture formed in its respective support leg so that liquid may flow through the element (56) into the element (58), the latter then being observed to detect a color change.

With further reference to the device of FIG. 12, the choice and location of reactants may be varied as desired.

The device shown in FIGS. 12-15 may readily be used in an organic analysis to determine the amount of glucose in, for example, urine. Referring to FIG. 12, the bibulous element (56) may contain adenosine triphosphate ("ATP") in a predetermined amount, and the enzyme hexokinase. Bibulous element (54) contains a detection system comprising a chromogen such as o-dianisidine, glucose oxidase and horseradish peroxidase as a signal generator that is sensitive to the presence of glucose. Element (58) contains glycerol, Methylene Blue, glycerol kinase and glycerol phosphate dehydrogenase. ATP added to the system causes reduction of the indicator Methylene Blue such that the indicator becomes colorless in the presence of a given, stoichiometrically sufficient quantity of ATP.

The present assay can be used to determine whether the concentration of glucose in a body fluid such as urine or blood is above or below the "normal" range. The detection system in element (54) is capable of detecting even quite small quantities of glucose; hence, the amount of ATP contained in the bibulous element (56) is made sufficient to react with all of the glucose in a test sample assuming the glucose concentration to be at the upper end of the "normal" range. If the concentration of glucose in the liquid sample added to the bibulous element (56) were at the lower end of the "normal" range, however, reaction of that quantity of glucose with the ATP would result in the presence of excess or unused ATP in the element (56). Hence, the quantity of Methylene Blue indicator dye in the bibulous element (58) is made sufficiently large as to tolerate the addition of the "excess" ATP, without becoming completely oxidized to its colorless leuco form. The presence of glucose in the liquid specimen at a concentration below the "normal" range results in the availability of additional ATP in the bibulous element (56), so that the ATP in this bibulous element is sufficient to oxidize the Methylene Blue indicator in the bibulous element (58). It will be understood that adjustments can be made to the concentrations of the various ingredients to allow for less than ideal transfer of glucose on the one hand or ATP on the other to the respective bibulous elements (54) and (58).

In use, a predetermined volume of liquid such as urine or blood plasma containing glucose is placed upon the bibulous element (56). The glucose reacts stoichiometrically with the ATP thereon in the presence of hexokinase, the reaction resulting in the presence of liquid-transferable excess glucose or excess ATP. The bibulous element (56), it will be noted, extends through the thickness of the strip upon which it is carried. The bibulous elements (54) and (58) are then simultaneously folded downwardly as shown in FIG. 15 upon opposite sides of the bibulous strip (56). Desirably, the bibulous elements (54) and (58) are far less absorbent than the bibulous element (56) so that the three reaction zones typified by the bibulous elements (56), (54) and (58) become in effect a substantially saturated single zone. Once equilibrium has been substantially reached, the bibulous elements (54), (58) can be returned to the position shown in FIG. 12, and observed for a color change. If the concentration of glucose in the physiological fluid was within the "normal" range, no change in color of the bibulous elements (54), (58) should be noted; that is, the element (54) should remain colorless and the element (58) should remain blue. If the glucose in the sample were below the normal range, then the dye indicator in the element (58) becomes reduced to its colorless leuco colorless form, both of the bibulous elements (54) and (58) then appearing colorless to a viewer. In the event that the glucose concentration was above the normal range, this fact is signaled by the appearance of a reddish-brown color in the bibulous strip (54).

Plastic material, such as polyethylene, has been typified in the foregoing examples as a suitable material for the support means that carries the respective bibulous elements and permits them to be brought into contact with one another by movement over a predetermined path. Various other materials may be used as well, of course, such materials including metals, coated papers, strips of glass (suitably hinged by an adhesive tape strip or the like, or held in an embodiment such as that shown in FIG. 7) and the like.

Thus, the instant invention provides an apparatus and method which can be rapidly used to indicate the presence, and, if desired, to approximate the amount, of a particular analyte. The apparatuses of the invention are simple to operate, and can be used generally in the field by non-technical personnel having a minimum of training. The internal referencing systems serve to indicate whether a particular test is in fact working. Devices of the invention, suitably enclosed in plastic wrappers or envelopes or the like, are expected to exhibit good storageability even under severe temperature conditions since storage occurs in the dry state. However, the internal referencing system as described may be employed to check the viability of stored products of the invention from time to time to assure their continued utility.

While preferred embodiments of the present invention have been described, it should be understood that various changes, adaptations and modifications may be made therein without departing from the spirit of the invention and the scope of the appended claims.

We claim:

1. Apparatus for the chemical analysis of an analyte comprising:
   A. a first bibulous element containing a chemical reaction system that includes all the reagents necessary to provide a liquid-transferable chemical species within the first element upon the addition of an analyte-containing liquid sample to the first element, the presence or amount of which species is related to the presence or amount, respectively, of analyte in the liquid sample;
   B. a second bibulous element containing a detection system responsive to the liquid-transferable chemical species to produce a perceptible signal; and
   C. support means carrying said bibulous elements in a normally spaced relationship but enabling one or both of the bibulous elements to move in a predetermined path to bring the elements into liquid transferring contact, thereby enabling any transferable chemical species to be transferred to the second bibulous element and reacted with the detection system to produce a perceptible signal.

2. The apparatus of claim 1 in which the support means supporting the second bibulous element is sufficiently transparent as to enable the perceptible signal to be perceived therethrough.

3. The apparatus of claim 1 wherein the support means supporting the first bibulous element includes conduit means enabling a liquid sample to pass therethrough into the first bibulous element.

4. The apparatus of claim 3 including a generally water-proof enclosure having ports therein adjacent the support means and positioned to permit the direct addition of a liquid sample to the first bibulous strip through said conduit means.

5. The apparatus of claim 1 wherein said chemical reaction system comprises a member of a ligand-receptor pair, of which the analyte is a pair member, uniformly bound to the first bibulous element and a labeled ligand-receptor pair member chosen to bind to the bound member of the ligand-receptor pair or to analyte bound thereto in relation to the quantity of analyte in said liquid sample and wherein the second bibulous element includes a label detection system responsive to said label to produce a detectable signal.

6. The apparatus of claim 1 wherein said chemical reaction system comprises a member of the ligand-receptor pair, of which the analyte is a member, uniformly bound to the first bibulous element and the liquid-transferable chemical species is a labeled ligand-receptor pair member chosen to bind to the bound member of the ligand-receptor pair or to analyte bound thereto in relation to the quantity of analyte in said sample and the second bibulous element includes a label detection system responsive to said label to produce a detectable signal.

7. Apparatus for detecting an analyte in a liquid sample, comprising first and second separate reaction zones, the first zone including a first bibulous element and containing a chemical reaction system that includes all the reagents necessary to provide a liquid-transferable chemical species within the first bibulous element upon the addition of an analyte-containing liquid sample to the first element, the presence or amount of which species is related to the presence or amount, respectively, of analyte in the liquid sample, and the second reaction zone including a second bibulous element carrying a chemical reaction system responsive to the transferable chemical species to produce a visually perceptible signal; and support means carrying the reaction zones and spacing the bibulous elements in adjacent, opposed, facing, aligned orientation and enabling the elements to move into liquid-transferring contact with one another.

8. The apparatus of claim 7 wherein the support means supporting the second bibulous element is sufficiently transparent as to enable the visually perceptible signal to be visually perceived therethrough.

9. The apparatus of claim 8 in which the support means includes conduit means extending through its thickness and enabling a liquid sample to pass therethrough into the first bibulous element.

10. The apparatus of claim 9 wherein the first zone includes a third bibulous element carried by the support means in liquid-transferring contact with the first bibulous element and positioned to be contacted by the liquid sample passing through said conduit.

11. Apparatus for the chemical analysis of an analyte, comprising first and second reaction zones, the first zone including a first bibulous element and containing a chemical reaction system that includes all the reagents necessary to provide a liquid-transferable chemical species within the first bibulous element upon the addition of an analyte-containing liquid sample to the first reaction zone, the presence or amount of which species is related to the presence or amount, respectively, of analyte in the liquid sample, and the second reaction zone including a second bibulous element containing a chemical detection system responsive to the transferable chemical species to produce a visually perceptible signal, the apparatus including first and second support strips carrying the respective first and second reaction zones, and connection means connecting the first and second strips and orienting the same in spaced, generally parallel planes with the bibulous elements carried in aligned, facing, and spaced relationship to one another, the support strips and connector means being so constructed and arranged as to enable the support strips to be manually pinched towards one another to bring the respective bibulous elements into liquid-transferring contact, the second support strip being transparent to enable the visually perceptible signal to be viewed therethrough.

12. A method for detecting an analyte that is a member of a ligand-receptor pair contained in a liquid sample, the method employing;

(a) a first reaction zone comprising a bibulous element and having bound thereto a member of the ligand-receptor pair;
(b) a labeled ligand-receptor pair member chosen to bind to the bound member of the ligand-receptor pair or to analyte bound thereto in relation to the quantity of analyte in the liquid sample, the label being part of a signal-producing system;
(c) a second reaction zone comprising a bibulous element carrying a label detection system responsive to said label to produce a detectable signal; and
(d) support means supporting said reaction zones in a normally spaced relationship but enabling one or both of the reaction zones to be moved in a predetermined path to bring the bibulous elements thereof into liquid-transferring contact;

said method comprising:

adding, to the first reaction zone, the liquid sample containing analyte and the labeled ligand-receptor pair member, the amount of the latter member remaining unbound and liquid-transferable in said first reaction zone relating to the presence or quantity of analyte in said liquid sample;

waiting a predetermined amount of time;

moving one or both of said reaction zones in said predetermined path to bring said bibulous elements into liquid-transferring contact with one another, permitting any unbound labeled ligand-receptor pair member to transfer to the second reaction zone, the detection system in the latter producing a detectable signal in response thereto; and detecting said signal.

13. A method for detecting an analyte in a liquid sample comprising the steps of:

(a) combining, in a first bibulous element a liquid sample and all the reagents necessary to react with analyte in the sample to provide a liquid-transferable chemical species within the first bibulous element, the quantity of said liquid-transferable species provided being related to the amount of analyte in the sample;
(b) after a predetermined amount of time moving the first bibulous element along a predetermined path into liquid-transferring contact with a second bibulous element containing a detection system responsive to the liquid-transferable chemical species to produce a perceptible signal; and
(c) perceiving said signal.

14. The method of claim 13 further comprising moving a third bibulous element containing a detection system responsive to the liquid-transferable chemical species to produce a perceptible signal along a predetermined path into liquid-transferring contact with the first bibulous element of the first reaction zone to bring the first and third bibulous elements into liquid-transferring contact independently of bringing the first and second bibulous elements together and perceiving a signal produced by the detection system of the third bibulous element independently of perceiving the signal produced by the detection system of the second bibulous element.

15. The method of claim 14 wherein said second elements are moved sequentially into contact with the first bibulous element.

16. The method of claim 14 wherein said second bibulous elements are simultaneously moved into contact with the first bibulous element.

17. The method of claim 14 in which said first bibulous element contains adenosine triphosphate (ATP) and hexokinase which reacts with glucose to provide a liquid-transferable species that is glucose or ATP, the detection system of the second bibulous element comprises o-dianisidine, glucose oxidase and horseradish peroxidase which together react with glucose to produce a perceptible signal and the detection system of the third bibulous element comprises Methylene Blue, glycerol kinase, glycerol and glycerol phosphate dehydrogenase which together react with ATP to produce a perceptible signal, the method further comprising the step of adding to the first bibulous element a liquid sample suspected of containing glucose.

* * * * *